United States Patent [19]

Colmenares

[11] Patent Number: 5,030,607

[45] Date of Patent: Jul. 9, 1991

[54] CATALYSTS FOR SYNTHESIZING VARIOUS SHORT CHAIN HYDROCARBONS

[75] Inventor: Carlos Colmenares, Alamo, Calif.

[73] Assignee: The United States of America as represented by the United States Department of Energy, Washington, D.C.

[21] Appl. No.: 347,765

[22] Filed: May 5, 1989

[51] Int. Cl.$^5$ .................. B01J 21/00; B01J 23/10; B01J 23/12

[52] U.S. Cl. .................. 502/240; 502/263; 502/300; 502/302; 502/304; 502/350; 502/351

[58] Field of Search ............... 502/232, 240, 300, 302, 502/304, 263, 350, 351

[56] References Cited

U.S. PATENT DOCUMENTS

| | | | |
|---|---|---|---|
| 2,378,530 | 6/1945 | Bailie et al. | 502/240 |
| 3,140,148 | 7/1964 | Hofer et al. | 502/300 |
| 3,649,169 | 3/1972 | Nicklin et al. | 502/300 |

FOREIGN PATENT DOCUMENTS 1154483  6/1969  United Kingdom ............... 502/240

OTHER PUBLICATIONS

*F87 Institutional Research and Development*, Lawrence Livermore National Laboratory document UCRL-536-89-87, p. 16, "Photoactivated Heterogeneous Catalysis on Aerogels".

"Inorganic Oxide Aerogels", by Teichner et al., *Advances in Colloid and Interface Science*, 5(1976), pp. 245–273.

"Partially Hydrolyzed Alkozysilanes as Precursors for Silica Aerogels", by Tillotson et al., Lawrence Livermore National Laboratory document UCRL-97434 (preprint) (1988).

"Preparation and Catalytic Properties of Supported Metal or Metal-Oxide on Inorganic Oxide Aerogels", by Astier et al., *Preparation of Catalysts*, Elsevier Scientific Publishing Company, The Netherlands, pp. 315–330 (1976).

"Methanation and Photo-Methanation of Carbon Dioxide at Room Temperature and Atmospheric Pressure", by Thampi et al., *Nature*, vol. 327, Jun. 11, 1987, pp. 506–508.

*The Chemistry of Uranium* by Joseph J. Katz et al., pp. 274–275 (1950).

"Oxidation Mechanisms and Catalytic Properties of the Actinides" by C. A. Colmenares, *Prog. Solid St. Chem.*, vol. 15, pp. 352–355 (1984).

*Introduction to Solid State Physics* by Charles Kittel, pp. 353–354 (1954).

*Primary Examiner*—Carl F. Dees
*Attorney, Agent, or Firm*—Henry P. Sartorio; L. E. Carnahan; William R. Moser

[57] ABSTRACT

Method and apparatus (10), including novel photocatalysts, are disclosed for the synthesis of various short chain hydrocarbons. Light-transparent $SiO_2$ aerogels doped with photochemically active uranyl ions (18) are fluidized in a fluidized-bed reactor (12) having a transparent window (16), by hydrogen and CO, $C_2H_4$ or $C_2H_6$ gas mixtures (20), and exposed to radiation (34) from a light source (32) external to the reactor (12), to produce the short chain hydrocarbons (36).

12 Claims, 1 Drawing Sheet

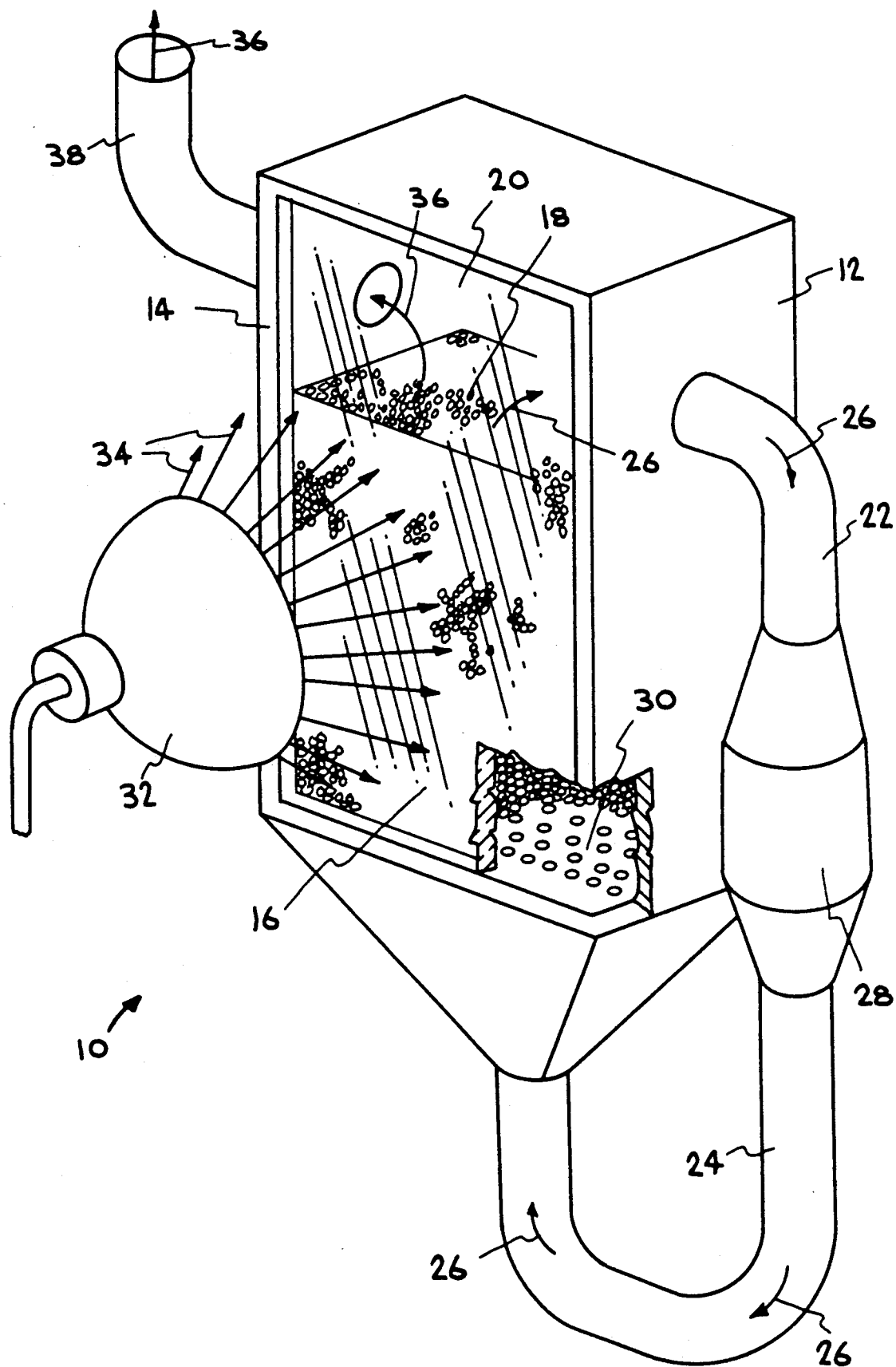

CATALYSTS FOR SYNTHESIZING VARIOUS SHORT CHAIN HYDROCARBONS

The U.S. Government has rights to this invention pursuant to Contract No. W-7405-ENG-48 between the U.S. Department of Energy and the University of California, for the operation of the Lawrence Livermore National Laboratory.

BACKGROUND OF THE INVENTION

The invention described herein relates generally to the catalytic synthesis of hydrocarbons, and more particularly to the photocatalytic hydrogenation of compounds such as ethane, ethylene, and carbon monoxide to various short chain hydrocarbons.

The very well known Fischer-Tropsch process for the synthesis of hydrocarbons by the catalytic hydrogenation of carbon monoxide, was discovered in 1923 in Germany. The Fischer-Tropsch reaction is very exothermic, and must be carried out in a reactor designed for adequate heat removal, to control temperature and avoid catalyst deterioration and carbon formation.

Astier et al discuss the "Preparation and Catalytic Properties of Supported Metal or Metal-Oxide on Inorganic Oxide Aerogels," in "Preparation of Catalysts," edited by Delmon et al, Elsevier Scientific Publishing Company, The Netherlands, pages 315 to 330 (1976).

Thampi et al teach the photo-methanation of carbon dioxide, in Nature, Volume 327, pages 506 to 508, 11 June 1987. The catalyst used was highly dispersed Ru/-RuO$_x$ loaded onto TiO$_2$, with the reaction rate being sharply enhanced through photo-excitation of the support material.

A review of fluidized-bed chemical processes is provided by Yates in "Fundamentals of Fluidized-bed Chemical Process", Butterworths Monographs in Chemical Engineering (1983), which text is incorporated by reference herein. An important application of fluidization has been in the catalysis of gas reactions, where the excellent opportunity of heat transfer and mass transfer, between catalytic surfaces and the gas stream, gives an extremely good performance.

Nonetheless, the problem remains of providing inventive and improved methods and apparatus for the catalytic hydrogenation of compounds such as ethane, ethylene, and carbon monoxide to various short chain hydrocarbons, such as $C_1$ to $C_8$ hydrocarbons, that particularly can be carried out at, or sightly above, room temperature.

SUMMARY OF THE INVENTION

It is, therefore, an object of the invention to provide method and apparatus for the catalytic synthesis of hydrocarbons.

Another object of the invention is to provide apparatus and methods, that can be carried out at or slightly above room temperature, and that can be empowered by sunlight, for the hydrogenation of compounds such as ethane, ethylene, and carbon monoxide to various short chain hydrocarbons, such as $C_1$ to $C_8$ hydrocarbons.

Yet another object of the invention is to provide improved and inventive catalysts for the synthesis of hydrocarbons.

Additional objects, advantages and novel features of the invention will be set forth in part in the description which follows, and in part will become apparent to those skilled in the art upon examination of the following or may be learned by practice of the invention The objects and advantages of the invention may be realized and attained by means of the instrumentalities and combinations particularly pointed out in the appended claims.

To achieve the foregoing and other objects and in accordance with the purpose of the present invention, as embodied and broadly described herein, a method for synthesizing quantities of various short chain hydrocarbons is provided wherein ground, light-transparent inorganic aerogel doped with catalytic photochemically active ions, such as ground and sieved SiO$_2$ aerogel doped with UO$_2^{2+}$, is placed in a fluidized-bed reactor. The doped aerogel is fluidized with a gas mixture comprised of hydrogen together with a compound selected from the group consisting of CO, $C_2H_4$ and $C_2H_6$. The fluidized doped aerogel is illuminated with light, that may often preferably be solar sunlight, having wavelengths in the range extending from approximately 0.2 to 3.0 microns. The quantities of short chain hydrocarbons are photocatalytically produced, and extracted from the fluidized-bed reactor.

Preferably the UO$_2^{2+}$ doped SiO$_2$ aerogel has a density within the approximate range extending from 50 to 300 milligrams per cubic centimeter; has a UO$_2^{2+}$ weight percentage within the approximate range extending from 0.1 to 0.5 weight percent; and is ground and sieved to a mesh value within the approximate range extending from 400 to 250 mesh.

The fluidizing gas mixture, preferably, has a hydrogen to CO gram molecule or volume ratio within the approximate range from 1.0 to 2.0; a hydrogen to $C_2H_4$ gram molecule or volume ratio within the approximate range from 1.0 to 2.0; or a hydrogen to $C_2H_6$ gram molecule or volume ratio within the approximate range from 1.0 to 2.0.

At times, the light source for illuminating the fluidized UO$_2^{2+}$ doped SiO$_2$ aerogel is preferably a mercury-xenon solar-illuminator lamp, preferably having a power within the approximate range from 200 to 1,000 watts, per gram of doped aerogel.

In a further aspect of the invention, the photoactivated catalysts used in the practice of this invention, as comprised of UO$_2^{2+}$ doped SiO$_2$ aerogel, are particularly pointed out as important components of this invention. Preferably, these inventive photocatalysts are ground and sieved to a mesh value within the approximate range extending from 400 to 250 mesh; have a density within the approximate range extending from 50 to 300 milligrams per cubic centimeter; and have a weight percent within the approximate range extending from 0.1 to 0.5 weight percent.

In yet another aspect of the invention, the inventive apparatus, for synthesizing various short chain hydrocarbons, of this invention, comprises a fluidized-bed reactor, for holding ground and sieved SiO$_2$ aerogel that is doped with UO$_2^+$. At least a portion of the external wall of the reactor is transmissive to radiation having wavelengths in the approximate range extending from 0.2 to 3.0 microns. Means are provided for using a gas mixture, comprised of hydrogen and a compound selected from the group consisting of CO, $C_2H_4$ and $C_2H_6$, to fluidize the doped aerogel. Sunlight or a radiation source, preferably a mercury-xenon solar-illuminator lamp, is used to illuminate the doped aerogel when it is fluidized by the gas mixture, with the light passing through the transmissive portio of the external wall of the reactor, that preferably, is comprised of quartz or sapphire. Means are provided for extracting the short chain hydrocarbons from the fluidized-bed reactor.

The benefits and advantages of the present invention, as embodied and broadly described herein, include, inter alia, novel photocatalysts, together with apparatus and methods that can be empowered by sunlight and carried out at or slightly above room temperature, for the photocatalytic synthesis of short chain hydrocarbons, including $C_1$ to $C_8$ hydrocarbons, by the hydrogenation of ethane, ethylene, and carbon monoxide.

BRIEF DESCRIPTION OF THE DRAWING

The accompanying drawing, which is incorporated in and forms a part of this specification, illustrates an embodiment of this invention and, together with the description, serves to explain the principles of this invention.

The Figure is a schematic, perspective view of an apparatus for synthesizing various short chain hydrocarbons, made in accordance with the invention.

DETAILED DESCRIPTION OF THE INVENTION

This invention comprises the use of light-transparent, inorganic aerogels that are catalytically doped with photochemically active ions, to provide new and unique catalysts, that may be fluidized by hydrogen and carbon monoxide or hydrocarbon compound gas mixtures, within fluid bed reactors having light-transmissive walls, in the presence of externally provided photon radiation, that may be in the form of sunlight, to stimulate the synthesis of various short chain hydrocarbons, including $C_1$ to $C_8$ hydrocarbons, under approximately room temperature conditions. Being light-transparent, the fluidized mass of doped aerogel catalyst may constantly be photochemically activated at virtually all locations simultaneously, by sunlight or lamplight introduced through the light-transmissive wall of the fluidized-bed reactor, to provide an extraordinarily abundant and extensive hydrocarbon synthesis yield.

The presently preferred, and novel, photoactive catalyst for use in this invention is $SiO_2$ aerogel doped with the uranyl ion $UO_2^{2+}$. However, it is anticipated that other photochemically doped inorganic aerogels may ultimately prove to be quite beneficial in a variety of hydrocarbon synthesis, and other uses. Although not specifically described, $UO_2^{2+}$ doped $SiO_2$ aerogels may be prepared by the methods and procedures enablingly set forth by Teichner et al, in "Inorganic Oxide Aerogels", in "Advances in Colloid and Interface Science", volume 5, pages 245 to 273 (1976), published by Elsevier Scientific Publishing Company, Amsterdam, The Netherlands, and by Tillotson et al, in "Partially Hydrolyzed Alkoxysilanes As Precursors For Silica Aerogels", Lawrence Livermore National Laboratory Document UCRL-97434 (Preprint) (1988), which documents are incorporated by reference herein. As clearly explained by Tillotson et al, silica aerogels are formed from alcogels, with alcogels being prepared from first mixtures comprised of partially condensed silica (tetramethylorthosilicate or tetraethylorthosilicate reacted with water) and a solvent, into which are slowly added second mixtures comprised of water, solvent and a catalyst which, to produce $UO_2^{2+}$ doped $SiO_2$ aerogels, is uranyl nitrate, $UO_2(NO_3)_2$. For use in this invention, it is presently preferred that the doped $SiO_2$ aerogel be ground and sieved to a mesh value within the approximate range extending from 400 to 250 mesh; have a density within the approximate range extending from 50 to 300 milligrams per cubic centimeter; and, have a $UO_2^{2+}$ weight percent within the approximate range extending from 0.1 to 0.5 weight percent.

Reference is now made in detail to the present preferred embodiment of the invention, as illustrated in the accompanying drawing. The Figure provides a schematic and perspective view of an apparatus 10 for synthesizing varius short chain hydrocarbons, including $C_1$ to $C_8$ hydrocarbons, in accordance with the invention. Apparatus 10 comprises a fluidized-bed reactor 12, having an external wall 14, with wall 14 having a radiation-transmissive window portion 16, that is transmissive to radiation having wavelengths in the range extending from approximately 0.2 to 3.0 microns. It is often preferred that window 16 be comprised of quartz or sapphire. Fluidized-bed reactors, such as fluidized-bed reactor 12, are very well known in the chemical, and related arts, and are extensively described, in addition to the Yates reference, cited above, by Cheremisinoff et al in "Hydrodynamics of Gas-Solids Fluidization", Gulf Publishing Company (1984), and by Geldart (Editor) in "Gas Fluidization Technology", John Wiley and Sons (1986), all of which are incorporated by reference herein. The fluidized-bed reactor 12 contains a quantity of ground and sieved, $UO_2^{2+}$ doped $SiO_2$ aerogel 18, as described above. It is pointed out that, because of its low density, a small mass of doped aerogel fills an apparently large volume.

A gas mixture 20, comprised of hydrogen together with a compound selected from the group consisting of CO, $C_2H_4$ and $C_2H_6$, is prepared by elementary means that are very well known in the chemical and related arts, and introduced into the fluidized-bed reactor 12. The preferred ratio of hydrogen to CO, by gram molecule or volume, is within the approximate range extending from 1.0 to 2.0. The preferred ratio of hydrogen to $C_2H_4$, by gram molecule or volume, is within the approximate range extending from 1.0 to 2.0. The preferred ratio of hydrogen to $C_2H_6$, by gram molecule or volume, is within the approximate range extending from 1.0 to 2.0. The gas mixture 20 is repetitively circulated through the fluidized-bed reactor 12, and a pair of related pipes 22 and 24, in the direction indicated by a multiplicity of arrows 26, by means of a gas pump 28. It is particularly pointed out that in other, very beneficial embodiments of this invention, gas mixtures, such as gas mixture 20, may be passed through fluidized-bed reactors, such as reactor 12, only one time in a single pass operation. Gas pumps, such as gas pump 28, are very well known in the chemical and related arts, and are routinely supplied by, for example the Metal Bellows Company of Sharon, Mass. The circulating gas mixture 20 passes through a distribution plate 30, which is a common and well known component of fluidized-bed reactors, and fluidizes the $UO_2^{2+}$ doped $SiO_2$ aerogel 18.

A radiation source 32, provides radiation having wavelengths in the range extending from approximately 0.2 to 3.0 microns, represented by a plurality of arrows 34, that passes through the radiation-transmissive window 16, and illuminates the $UO_2^{2+}$ doped $SiO_2$ aerogel 18, that is fluidized by the circulating gas mixture 20. Radiation source 32 is a mercury-xenon solar-simulation lamp, having a power, per gram of $UO_2^{2+}$ doped $SiO_2$ aerogel, within the approximate range extending from 200 to 1,000 watts. Such mercury-xenon solar-simulation lamps are very commonly available and supplied, for example, by the Oriel Corporation of Stratford, Conn. However, it is especially pointed out that in many very beneficial embodiments of the present invention, empowering radiation from the sun, that is, sunlight, is simply allowed to pass through the radiation-transmissive window 16, to illuminate the doped aerogel 18.

As the light from radiation source 32, represented by arrows 34, illuminates the $UO_2^{2+}$ doped $SiO_2$ aerogel photocatalyst 18 as it is being fluidized by the circulating hydrogen and compound gas mixture 20, a plurality of quantities of various short chain hydrocarbons, including $C_1$ to $C_8$ hydrocarbons, as explained hereinbelow and as represented by arrows 36, is synthesized and extracted from the fluidized-bed reactor 12, by and through means schematically represented by an extraction pipe 38. The means for the extraction of gaseous product from fluidized-bed reactors, such as reactor 12, and the subsequent chemical separation, storage and utilization thereof are very well known in the chemical, and related, arts as explained in many articles and texts such as, for example, the "Kirk-Othmer Encyclopedia of Chemical Technology, Third Edition", published since 1978 by John Wiley and Sons, New York, which is incorporated by reference herein.

As examples, in very preliminary experiments, approximately 0.5 gram quantities of $SiO_2$ aerogel doped with an approximately 0.45 weight percent of $UO_2^{2+}$ ion, having densities within the inclusive range extending from 50 to 100 milligrams per cubic centimeter, and ground and sieved to 300 mesh, were separately fluidized, in fluidized-bed reactors having quartz walls, by one of three gas mixtures, while being continuously illuminated by light from 1000 watt, mercury-xenon solar-illuminator lamps. The three gas mixtures were two parts of hydrogen to one part of CO, by gram molecule or volume; one part of hydrogen to one part of $C_2H_4$, by gram molecule or volume; and, one part of hydrogen to one part of $C_2H_6$, by gram molecule or volume. In each of these experiments various short chain hydrocarbons were synthesized, as shown in the following Table.

TABLE

| | $H_2$/CO | $H_2$/$C_2H_4$ | $H_2$/$C_2H_6$ |
|---|---|---|---|
| $C_1$ | methane | methane | methane |
| $C_2$ | ethane, ethylene | ethane | ethylene |
| $C_3$ | propane | propane | (none observed) |
| $C_4$ | butane, isobutane | butane | (none observed) |
| $C_5$ | pentane | pentane | (none observed) |
| $C_6$ | hexane | hexane | (none observed) |
| $C_7$ | heptane | heptane | (none observed) |
| $C_8$ | octane | octane | (none observed) |

In each of these preliminary experimental examples, the fluidized-bed reached a temperature of only approximately 90 degrees centigrade, which is at, or only slightly above, room temperature. When several experiments exactly as described above were repeated, except without illumination from mercury-xenon solar-illuminator lamps, but with externally heating the contents of the fluidized-bed reactors to temperatures of approximately 100 and 200 degrees centigrade, only negligible quantities of synthesis product were detected. In yet another preliminary experiment, using only $SiO_2$ aerogel that was not doped with $UO_2^{2+}$ ion, but with mercury-xenon solar-illuminator lamp illumination, $C_1$ and $C_2$ hydrocarbons, and an unidentified product, in quantities about ten times lower than when $UO_2^{2+}$ doped $SiO_2$ aerogel is used, were observed.

It is thus appreciated that in accordance with the invention as herein described and shown in the Figure, novel photocatalysts together with apparatus and methods that can be empowered by sunlight and carried out at or slightly above room temperature, for the photocatalytic synthesis of short chain hydrocarbons, including $C_1$ to $C_8$ hydrocarbons, by the hydrogenation of CO, $C_2H_4$ and $C_2H_6$, are provided.

The described embodiment of the invention has been presented for purposes of illustration and description. It is not intended to be exhaustive or to limit the invention to the precise form disclosed, and obviously many modifications and variations are possible in light of the above teaching. For example, $SiO_2$ aerogel doped with iron, cerium or europium, as well as $Al_2O_3$ or $ThO_2$ aerogels doped with uranyl ions, iron, cerium or europium, may collectively or individually prove to be very effective photocatalysts in methods and apparatus similar to the present invention. Additionally, $TiO_2$ or other photochemically active oxides or elements may be incorporated into aerogels, and used to catalyze various reactions, either as herein described, or of a different nature. Also, sunlight filtered to selected wavelengths may be used to empower specifically desired catalytic reactions. Further, sunlight empowered, catalyzed fluidized-beds of immense size, may be envisioned and are to be subsumed under the present invention.

The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. A photoactive catalyst, for use in synthesizing short chain hydrocarbons, comprising $SiO_2$ aerogel doped with $UO_2^{2+}$.

2. A photoactive catalyst, as recited in claim 1, wherein the $SiO_2$ aerogel doped with $UO_2^{2+}$ is ground and sieved to a mesh value within the approximate range extending from 400 to 250 mesh; has a density within the approximate range extending from 50 to 300 milligrams per cubic centimeter; and, has a $UO_2^{2+}$ weight percent within the approximate range extending from 0.1 to 0.5 weight percent.

3. A photoactive catalyst comprising a light-transparent, inorganic aerogel doped with catalytic photochemically active ions.

4. The catalyst of claim 3 wherein the aerogel is selected from $SiO_2$, $Al_2O_3$ and $ThO_2$ aerogels.

5. The catalyst of claim 3 wherein the photochemically active ions are selected from iron, cerium, europium, and uranyl ions.

6. The catalyst of claim 4 wherein the photochemically active ions are selected from iron, cerium, europium, and uranyl ions.

7. A photoactive catalyst comprising a light-transparent, inorganic aerogel doped with a photochemically active oxide.

8. The catalyst of claim 7 wherein the aerogel is selected from $SiO_2$, $Al_2O_3$ and $ThO_2$ aerogels.

9. The catalyst of claim 7 wherein the oxide is $TiO_2$.

10. The catalyst of claim 8 wherein the oxide is $TiO_2$.

11. The catalyst of claim 3 wherein the aerogel is transparent to light with wavelengths in the range of about 0.2 to about 3.0 microns.

12. The catalyst of claim 7 wherein the aerogel is transparent to light with wavelengths in the range of about 0.2 to about 3.0 microns.

* * * * *